United States Patent [19]
Todd et al.

[11] Patent Number: 6,005,127
[45] Date of Patent: Dec. 21, 1999

[54] ANTIMONY/LEWIS BASE ADDUCTS FOR SB-ION IMPLANTATION AND FORMATION OF ANTIMONIDE FILMS

[75] Inventors: Michael A. Todd, Danbury; Thomas H. Baum, New Fairfield; Gautam Bhandari, Danbury, all of Conn.

[73] Assignee: Advanced Technology Materials, Inc., Danbury, Conn.

[21] Appl. No.: 08/977,507

[22] Filed: Nov. 24, 1997

[51] Int. Cl.$^6$ ........................................................ C07F 9/70
[52] U.S. Cl. ................................ 556/70; 556/64; 556/71
[58] Field of Search ................................. 556/64, 70, 71

[56] References Cited

PUBLICATIONS

CA:73:89035 ab of DE1960732, Aug. 1970.
CA:81:38278 abs of Mater. Soveshch. Mekh, Ingibirovaniya Tsepnykh Gazov Reakts 1st Meeting date 1970 229–35 pp by Ksandopulo, 1971.
CA:107:108097 abs of India Acta Cienc Indica Chem 12(2) pp. 96–99 by Dwivedi, 1986.
CA:88179766 abs by Kyuntsel in Koord Khim 3(7) pp. 1035–1038, 1977.
Chem abstracts 1959:13786d, 1959.
CA:82:65165 by Mente Inorg Chem 14(1), pp. 123–126, 1975.
Chem Reviews by Jensen "The Lewis Acid–Base definitions", vol. 78, No. 1 pp. 1–22, Feb. 1978.
"Advanced Organic Chemistry" by Mar. 4th edition, pp. 260–272, 1992.
CA:113:114384 ab of CN 1032654, May 1989.
CA:113:96673 abs from J Fluorine Chem 46(2) pp. 265–281, 1990.
Database CAPLUS on STN, Chem Abstracts, (Columbus OH, USA) No. 129:237793, Todd, M. et al. Novel antimony precursors for low–temperature CVD of antimonide thin films. Mater. Res. Soc. Sump. Proc. Abstract. Apr. 1998, vol. 495, pp. 113–118.
Database CAPLUS on STN, Chem Abstract (Columbus OH, USA) No 89:15388, Sugiura, H. 'A method of silicon vacuum deposition combined with antimony ion implantation.' Skinku. Abstract, Mar. 1978, 21(3), pp. 80–85.
Database CAPLUS on STN, Chem Abstract (Columbus OH, USA) No. 113:96673, Naumann, D. et al. 'Trifluoromethylation of furan, thiopene, pyrrole, and p–benzoquinone with CF3I, Te(CF3) 2, Sb (CF3) 3, Hg (CF3) 2, and Cd (CF3) 2.cntdot.D.' J. Fluorine Chem. (1990), 46 (2), pp. 265–281.
Database CAPLUS on STN, Chem Abstract (Columbus OH, USA) No 113:114384, Huang, Y., et al. 'Catalysts for alkenylation of aldehydes and their application.' Faming Zhuanli Shenqing Gongkai Shuomingshu, 12 pp.
Molnár, J., et al., "Molecular Structure of SbI$_3$ and BiI$_3$ from Combined Electron Diffractionand Vibrational Spectroscopic Studies," Inorg. Chem. 1996, 35, pp. 7639–7642.
Todd, M.A., et al., "Novel Antimony Precursors for Low–Temperature CVD of Antimonide Thin Films," Submitted at MRS Proceedings, Dec. 5, 1997.

Naumann, D., et al., "Polar trifluoromethylation reactions. Synthesis and NMR spectra of tris(trifluoromethyl)antimony, Sb(CF$_3$)$_3$," Journal of Organometallic Chemistry, 333 (1987) pp. 193–197.
Oleszek, G.M., et al., "Sb Implantation for Bipolar Buried Layers Using SbF$_5$ in a Cold–Cathode Implantation System," Nuclear Instruments and Method in Physics Research B6 (1985) pp. 389–393.
Wardell, J. L., "Arsenic, Antimony and Bismuth," University of Aberdeen, pp. 681–707.
Von Gerhart Jander, et al., "Geschmolzenes Antimon (III)–Bromid Als Ionisierendes Lösungsmittel Und Das Verhalten Darin Gelöster Substanzen.I," Aus dem Anorganisch–Chemischen Institut der Technischen Universität Berlin–Charlottenburg (Eingegangen am 29. Jul. 1957), pp. 1275–1283.
Cao, D. S., et al., "Decomposition Studies of Tertiarybutyldimethylantimony," Solid–State Electronics Laboratory (1991) pp. 583–588.
Dale, J. W., et al., "Organometallic and Organometalloidal Fluorine Compounds. Part XIII Trifluoromethyl Derivatives of Antimony," Presented at American chemical Society Meeting, New York, 1954, pp. 3708–3713.
Bigeleisen, J., et al., "Calculation of Equilibrium Constants for Isotopic Exchange Reactions," The Journal of Chemical Physics, vol. 15, No. 5, May 1947, pp. 261–267.
Breunig, H. J., et al., "Strukturen und Reaktionen von Methylantimondihalogeniden und Versuche zur Darstellung von Methylantimon," Journal of Organometallic Chemistry, 470 (1994) 87–92, pp. 87–92.
Sugiura, O., et al., "Low–Temperature Growth of InSb by Vacuum MOCVD Using TeIn and SbH$_3$," Journal of Electronic Materials, vol. 17, No. 1, 1988, pp. 11–14.
Romig, T., et al., "Advances in Ion Implanter Productivity and Safety," Solid State Technology, Dec. 1996, pp. 69–74.
Hendershot, D. G., et al., "Synthesis, Characterization, and Chemical Vapor Deposition Properties of Primary and Secondary Neopentylstibine. New Antimony Precursors for MOCVD," Chem. Mater. 1992, 4, 883–837.

(List continued on next page.)

*Primary Examiner*—Gary Geist
*Assistant Examiner*—Jean F. Vollano
*Attorney, Agent, or Firm*—Steven J. Hultquist; Oliver A. M. Zitzmann

[57] ABSTRACT

An antimony/Lewis base adduct of the formula SbR$_3$.L, wherein each R is independently selected from $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, substituted $C_6$–$C_{10}$ aryl and halo; and L is a Lewis base ligand coordinating with SbR$_3$. The adducts of the invention are useful as metal source compositions for chemical vapor deposition, assisted chemical vapor deposition (e.g., laser-assisted chemical vapor deposition, light-assisted chemical vapor deposition, plasma-assisted chemical vapor deposition and ion-assisted chemical vapor deposition), ion implantation, molecular beam epitaxy, and rapid thermal processing, to form antimony or antimony-containing films.

18 Claims, 5 Drawing Sheets

OTHER PUBLICATIONS

Halonen, M., et al., "Local–Mode Effects on the Rotational Structure of the First Stretching Overtone Band System of Stibine, $SbH_3$," J. Chemical Phys., 95(10), Nov. 15, 1991, pp. 7099–7107.

Hendershot, D. G., et al., "Primary and Secondary Trimethylsilylmethylstibines. Synthesis, Characterization and Chemical Vapor Depostion Properties," Journal of Organometallic Chemistry, 119 (1993) pp. 119–123.

Bailar, Jr., J. C., et al., "Antimony Triiodide," Inorganic Syntheses, pp. 104–105.

ANTIMONY/LEWIS BASE ADDUCTS FOR SB-ION IMPLANTATION AND FORMATION OF ANTIMONIDE FILMS

CROSS-REFERENCE TO RELATED APPLICATION

U. S. patent application Ser. No. 08/977,225 in the names of Michael A. Todd, Thomas H. Baum and Gautam Bhandari for "Stable Hydride Source Compositions for Manufacture of Semiconductor Devices and Structures" is being co-filed herewith on Nov. 24, 1997.

BACKGROUND OF THE INVENTION

1. Field of the Invention

This invention relates to antimony/Lewis base adducts useful as source reagents for applications including Sb-ion implantation and formation of antimonide films.

2. Description of the Related Art

In the fabrication of advanced semiconductor devices, processes such as III–V MOCVD and p/n doping by ion implantation ideally require the use of Group III and Group V hydrides.

However, the hydrides of the heavier elements of Group III and Group V are unstable or in some cases are simply not known. For instance, stibine is only stable at very low temperatures (−78° C.), decomposing spontaneously at room temperature, while indane cannot be isolated.

In addition, alkyl or aryl metal hydrides such as $HSbR_2$ and $H_2SbR$, wherein R is alkyl, are also unstable.

Although literature reports indicate that researchers have synthesized and used metal hydrides as precursors when stored at low temperatures, widespread commercialization has not been possible due to the limited stability of the hydrides to light, heat and metal surfaces (i.e., stainless steel). Sophisticated microelectronic components and device heterostructures are driving the development of CVD precursors that exhibit useful volatility and the ability to deposit high-purity films. Currently, many III–V devices based upon strained layer superlattices and multiple quantum wells (MQW) are fabricated by molecular beam epitaxy (MBE). MBE is relatively slow and expensive when compared to alternate thin-film growth techniques used for microelectronics.

Although chemical vapor deposition (CVD) offers a low-cost, high throughput approach to device manufacturing, a lack of suitable, low temperature CVD precursors has hindered its widespread applicability. This is particularly true for Sb-based heterostructures that display important optoelectronic and electronic properties, including InSb, InGaSb, InAsSb, GaAlSb and InSbBi. Volatile and thermally stable Sb precursors would facilitate the chemical vapor deposition of antimonide thin-films, as required for the large scale, controlled production of antimonide based lasers, detectors and microelectronic sensors.

Antimonide materials are attractive for commercial infrared optoelectronic applications. The compositional variety and stoichiometry of III–V compound semiconductors allows for nearly complete coverage of the infrared spectrum. Bandgaps ranging from 2.5 eV in AlP to 0.2 eV in InSb can be achieved by forming strained thin-films with the proper elemental and stoichiometric compositions. Materials of greatest interest include InSbBi and InAs-SbBi for long wavelength (8–12 mm) infrared detectors, InAsSb and InGaSbfor mid-infrared absorbers in military applications, and $InSb/In_{1-x}Al_xSb$ light emitting diodes (LEDs) for mid-infrared chemical sensor applications. Many of these materials, however, as mentioned above are metastable compositions that necessitate high-purity films and low processing temperatures.

Antimonides are also of great interest as semiconductor infrared lasers. For instance, a type-II quantum well superlattice laser, comprised of InAsSb active layer with alternating InPSb and AlAsSb cladding layers, provides 3.5 mm emission upon electron injection. Similarly, mid-infrared lasers comprised of InAs/InGaSb/InAs active regions with lattice-matching to AlSb cladding layers were also demonstrated. The device fabrication requires thin-film processing of elemental aluminum, antimony, gallium and indium to produce both the active and cladding layers, and thereby, presents a significant technological challenge. The inherent physical properties of Ga, Sb and In necessitate low processing temperatures to alleviate inter-diffusion, melting, and re-evaporation (i.e., InSb melts at 525° C.). Unfortunately, current Sb CVD sources, such as trimethyl antimony, require processing temperatures in excess of 460° C. to achieve precursor decomposition and useful film growth rates.

Additionally, if advances in DRAM storage density based upon current technology are to continue, it will be necessary to develop dopants that can be utilized in very shallow p/n layers. This implies that traditional dopants such as boron (p-type) and phosphorus (n-type) will have to be replaced due to their high mobility in silicon (which results in a breakdown of the junction, even with reduced thermal budgets).

Of further concern is the lack of accurate control of the implant profile obtained by using B and P. High implantation energies are utilized for these implant species since lower beam energies are difficult to achieve, as a result of beam instabilities and low beam currents characteristically obtained at lower energy conditions.

Given the fact that more massive fragments that may be used in ion implantation applications (such as $BF_2^+$) also have deleterious consequences on device performance, it has become increasingly apparent that alternative dopants are required.

The two logical choices for p- and n-type dopants are indium and antimony, respectively, due to their greater size and mass, which provide superior diffusion characteristics relative to traditional implant species. These properties make it is possible to use lower implant energies and more advantageous geometries when depositing the shallow p/n junctions that are critical to DRAM storage density increases. However, as mentioned previously herein, suitable volatile antimony and indium precursors are currently unavailable.

SUMMARY OF THE INVENTION

The present invention relates to antimony/Lewis base adducts having utility, inter alia, as source reagents for ion implantation of antimony and for formation of antimony or antimony-containing films by processes such as chemical vapor deposition, assisted chemical vapor deposition (e.g., laser, light, plasma, ion, etc.), ion implantation, molecular beam epitaxy, and rapid thermal processing.

Such antimony/Lewis base adducts may have the formula:

$$SbR_3 \cdot L$$

wherein:

each R is independently selected from $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, substituted $C_6$–$C_{10}$ aryl and halo; and L is a Lewis base ligand coordinating with $SbR_3$.

L may comprise any suitable Lewis base ligand which is compatible and complexes with $SbR_3$. Potentially useful Lewis base species in the broad practice of the present invention include, but are not limited to, (a) amines and polyamines;

(b) N, S and O-containing aromatics such as pyridine, including bipyridine;

(c) ligands of the formula:

wherein:

G is —O—, —S—, or —NR—, wherein R is H or hydrocarbyl, e.g., $C_1$–$C_8$ alkyl;

(d) crown ethers;

(e) thioethers; and (f) ligands of the formula: $R^0O(C(R^1)_2C(R^2)_2O)_nR^0$
wherein:

$R^0$=H, methyl, ethyl, n-propyl, cyanato, perfluoroethyl, perfluoro-n-propyl, or vinyl;

$R^1$=H, F, or a sterically acceptable hydrocarbyl substituent;

$R^2$=H, F, or a sterically acceptable hydrocarbyl substituent;

n=2,3,4,5, or 6; and each $R^0$, $R^1$, and $R^2$ may be the same as or different from the other $R^0$, $R^1$, and $R^2$, respectively.

Specific illustrative examples of ligand L include tetraglyme, tetrahydrofuran, bipydridine, ammonia, pyridine, 3-phenylpyridine, 3-picoline, 18-crown-6 ethers, and amines/polyamines such as pentamethyldiethylenetriamine (PMDETA), diethylenetriamine (DETA), tetraethylenepentaamine (TEPA) and hexamethyltetraethylenepentaamine (HMTEPA).

In one of the more specific aspects thereof, the present invention relates to tris(trifluoromethyl)stibine adducts of the formula:

$Sb(CF_3)_3 \cdot L$ wherein L is as described above.

In another aspect, the invention relates to a method of depositing antimony on a substrate from an antimony-containing precursor therefor, comprising using as a precursor an antimony/Lewis base adduct of the formula:

$SbR_3 \cdot L$ wherein:

each R is independently selected from $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloakyl, substituted $C_6$–$C_{10}$ aryl and halo; and L is a Lewis base ligand coordinating with $SbR_3$.

In such method, the antimony may be deposited by a process selected from the group consisting of chemical vapor deposition, assisted chemical vapor deposition (e.g., laser, light, plasma, ion, etc.), ion implantation, molecular beam epitaxy, and rapid thermal processing.

Still another aspect of the invention relates to a storage and dispensing system for an antimony source reagent, comprising:

a vessel containing (1) a sorbent material having sorptive affinity for the antimony source reagent and (2) the antimony source reagent;

wherein the antimony source reagent comprises an antimony/Lewis base adduct of the formula:

$SbR_3 \cdot L$ wherein:

each R is independently selected from $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, substituted $C_6$–$C_{10}$ aryl and halo; and L is a Lewis base ligand coordinating with $SbR_3$.

In such storage and dispensing system, the sorbent material may suitably comprise a solid physisorbent material. Alternatively, the sorbent material may comprise a liquid sorbent in which the antimony source reagent is soluble, such as polyethers, glycols, cryptanes and crown ethers.

Other aspects, features and advantages of the present invention will be more fully apparent from the ensuing disclosure and appended claims.

DETAILED DESCRIPTION OF THE INVENTION, AND PREFERRED EMBODIMENTS THEREOF

The present invention is based on the discovery of antimony/Lewis base adducts useful, inter alia, for ion implantation and thin film antimonide deposition.

The adducts of the invention are markedly less reactive towards oxygen than the parent antimony compounds, yet still retain useful volatility. This combination of properties makes the adducts of the present invention excellent source reagents for ion implant and chemical vapor deposition applications, because they are much safer to use than the parent molecule.

The antimony/Lewis base adducts of the invention have the formula:

$SbR_3 \cdot L$ wherein:

each R is independently selected from $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, substituted $C_6$–$C_{10}$ aryl and halo; and L is a Lewis base ligand coordinating with SbR$_3$.

As indicated, L may comprise any suitable Lewis base ligand which is compatible and complexes with SbR$_3$, e.g., (a) amines and polyamines;

(b) N, S and O-containing aromatics such as pyridine, including bipyridine;

(c) ligands of the formula:

wherein:

G is —O—, —S—, or —NR—, wherein R is H or hydrocarbyl, e.g., C$_1$–C$_8$ alkyl;

(d) crown ethers;

(e) thioethers; and (f) ligands of the formula: R$^0$O(C(R$^1$)$_2$C(R$^2$)$_2$O)$_n$R$^0$ wherein:

R$^0$=H, methyl, ethyl, n-propyl, cyanato, perfluoroethyl, perfluoro-n-propyl, or vinyl;

R$^1$=H, F, or a sterically acceptable hydrocarbyl substituent;

R$^2$=H, F, or a sterically acceptable hydrocarbyl substituent;

n=2,3,4,5, or 6; and each R$^0$, R$^1$, and R$^2$ may be the same as or different from the other R$^0$, R$^1$, and R$^2$, respectively.

The ligand L by way of example may be tetraglyme, tetrahydrofuran, bipydridine, ammonia, pyridine, 3-phenylpyridine, 3-picoline, 18-crown-6 ethers, and amines/polyamines such as pentamethyldiethylenetriamine (PMDETA), diethylenetriamine (DETA), tetraethylenepentaamine (TEPA) or hexamethyltetraethylenepentaamine (HMTEPA).

Tris(trifluoromethyl)stibine adducts of the formula:

wherein L is as described above, are particularly useful antimony source reagents.

The antimony source reagents of the invention may be employed to deposit antimony on a substrate, e.g., by a process such as chemical vapor deposition, assisted chemical vapor deposition (e.g., laser, light, plasma, ion, etc.), ion implantation, molecular beam epitaxy, or rapid thermal processing.

The synthesis of antimony source reagents of the invention may be effected by reacting the antimony compound SbR$_3$ with the Lewis base species L to yield the adduct, SbR$_3$.L. The antimony compound SbR$_3$ may in turn be formed from the corresponding halide SbX$_3$ by non-aqueous reaction to form the hydride, followed by reaction of the hydride with an alkylating or other functionalizing reagent, to form the antimony compound SbR$_3$. Alternatively, the halide SbR$_3$ may be directly reacted with the Lewis base, L, to form the adduct, SbR$_3$.L, by reactions such as:

SbX$_3$+H$_3$CNH$_2$→H$_3$CH$_2$N:SbX$_3$(s)

SbX$_3$+H$_3$CCH$_2$NH$_2$→H$_3$CCH$_2$H$_2$N:SbX$_3$(s).

where X=F, Cl, Br or I

As a still further synthesis alternative, antimony metal may be employed to prepare the adducts.

The liquid source adducts can be utilized for forming antimony or antimony-containing films on substrates by any suitable means and/or method, including for example liquid delivery chemical vapor deposition, wherein the liquid is vaporized and antimony is deposited on a substrate in a CVD reactor from the vapor phase of the vaporized precursor. Solid source reagents can be dissolved or suspended in a compatible solvent medium and likewise be employed in liquid delivery chemical vapor deposition, wherein the solution or suspension is vaporized and antimony is deposited on a substrate in a CVD reactor from the vapor phase of the precursor material. Alternatively, conventional bubbler techniques may be employed.

Illustrative of the Lewis-base adducts of the invention are adducts of Sb(CF$_3$)$_3$ with ammonia, pyridine and phenylpyridine. Related acid-base adducts may also be synthesized within the broad scope of the invention (e.g., species with a lone-pair of electrons capable of dπ-pπ backbonding with Sb such as Me$_2$O, NMe$_3$, etc.).

Figure 1:
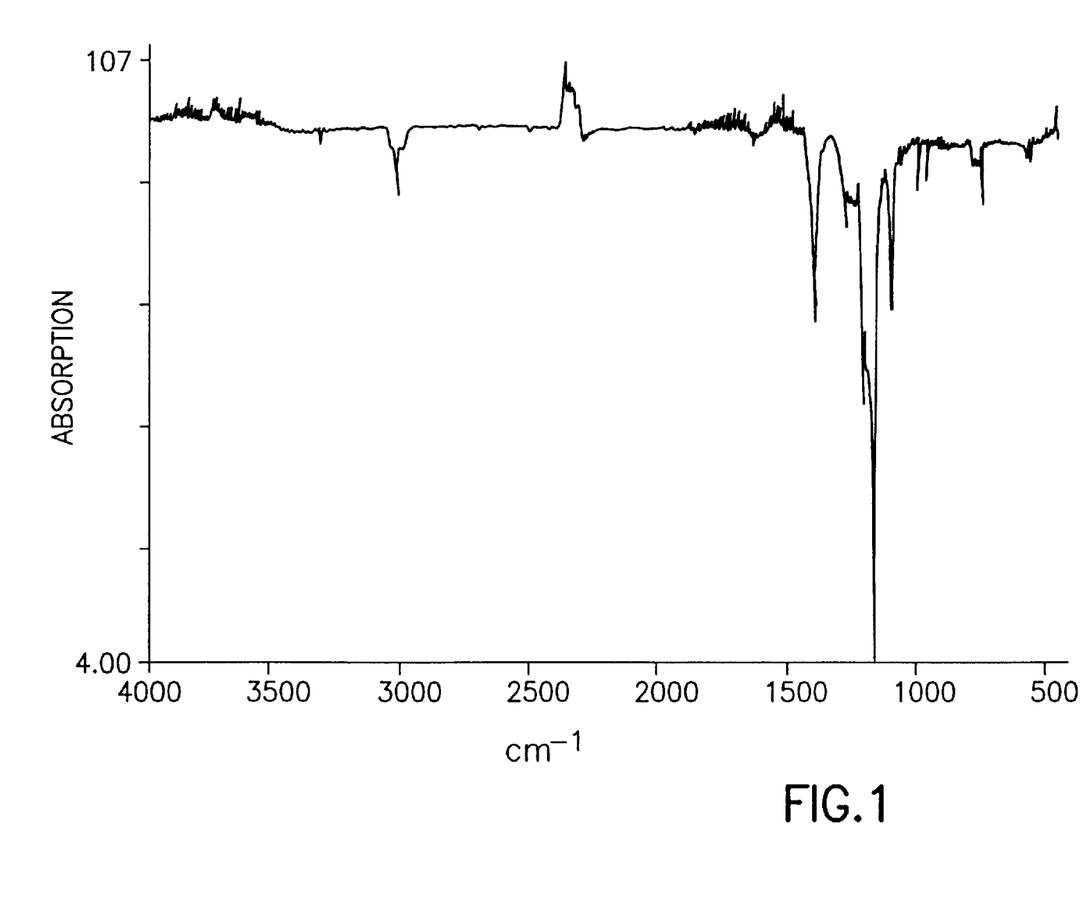
FIG. 1 shows a vapor phase FTIR spectrum of the tris(trifluoromethylstibine)-ammonia adduct.
Figure 2:
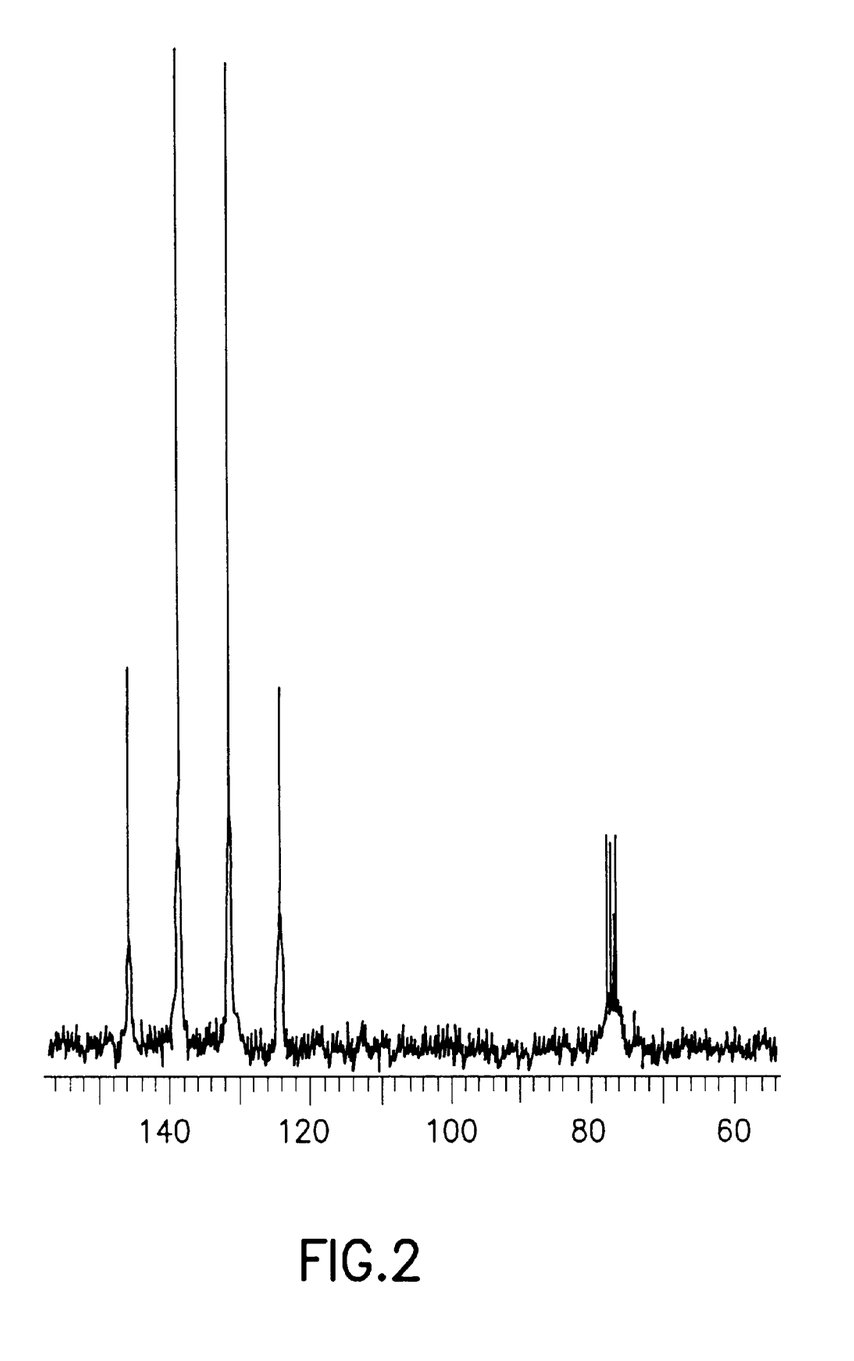
FIG. 2 shows a $^{13}C$ NMR spectrum of $Sb(CF_3)_3 \cdot NH_3$ evidencing a pronounced downfield shift of the carbon resonances of approximately 3 ppm from the unbound molecule.

A gas phase FTIR spectrum of an illustrative ammonia adduct, H$_3$N:Sb(CF$_3$)$_3$, is shown in FIG. 1 and the $^{13}$C NMR spectra of the adduct in CDCl$_3$ is shown in FIG. 2.

The FTIR spectrum shown in FIG. 1 clearly indicates that ammonia has been bound to Sb(CF$_3$)$_3$. This is evidenced by the shifts in the N—H and C—F stretching and bending modes, as well as by the reduced symmetry evidenced in the N—H stretch and NH$_3$ in-plane bending modes.

In the $^{13}$C NMR spectrum of the ammonia adduct shown in FIG. 2, there is a marked downfield shift in the resonances of the trifluoromethyl carbon atoms of approximately 3 ppm from the unbound molecule.

The tris(trifluoromethylstibine)ammonia adduct is a mobile colorless liquid with a room temperature vapor pressure of approximately 22 Torr suitable for use as a precursor both for ion implantation and for chemical vapor deposition because NH$_3$ is a thermally robust, carbon-free adduct that does not readily decompose at low temperature. The thermal stability of such adduct eliminates carbon or nitrogen contamination. In addition, the parent molecule, Sb(CF$_3$)$_3$, is known to thermally decompose at approximately 200° C., which is consistent with the ability of the adduct to enable high purity antimonide film growth at low processing temperatures.

Additionally, the adduct precursor molecule contains excellent leaving groups in the form of CF$_3$ radicals that can easily combine with each other to form hexafluoroethane, as a thermally stable low-temperature byproduct. Accordingly, the precursor H$_3$N:Sb(CF$_3$)$_3$ is a good source of pure Sb, with carbon contamination being kept to a minimum in use thereof.

As further illustrative examples of other Lewis-base adducts of the invention, H$_5$C$_5$N: Sb(CF$_3$)$_3$ and tris (trifluoromethylstibine)-3-phenylpyridine adduct may be usefully employed in CVD and ion-implantation applications.

$H_5C_5N{:}Sb(CF_3)_3$ is a stable, white solid that may be conveniently formed by the reaction of anhydrous pyridine with pure $Sb(CF_3)_3$. This low-melting, solid adduct (which melts at approximately 40–41° C.) has a vapor pressure of nearly 3 Torr at room temperature (25° C.) and displays a greatly reduced reactivity towards oxygen relative to the pure compound. For instance, the pure compound reacts explosively upon exposure to air, while the pyridine adduct merely fumes upon exposure. As with the ammonia adduct, this species may be usefully employed as a stable low-temperature source of antimony in CVD applications. The vapor phase IR spectrum of the adduct $H_5C_5N{:}Sb(CF_3)_3$ is shown in FIG. 3.

Figure 3:
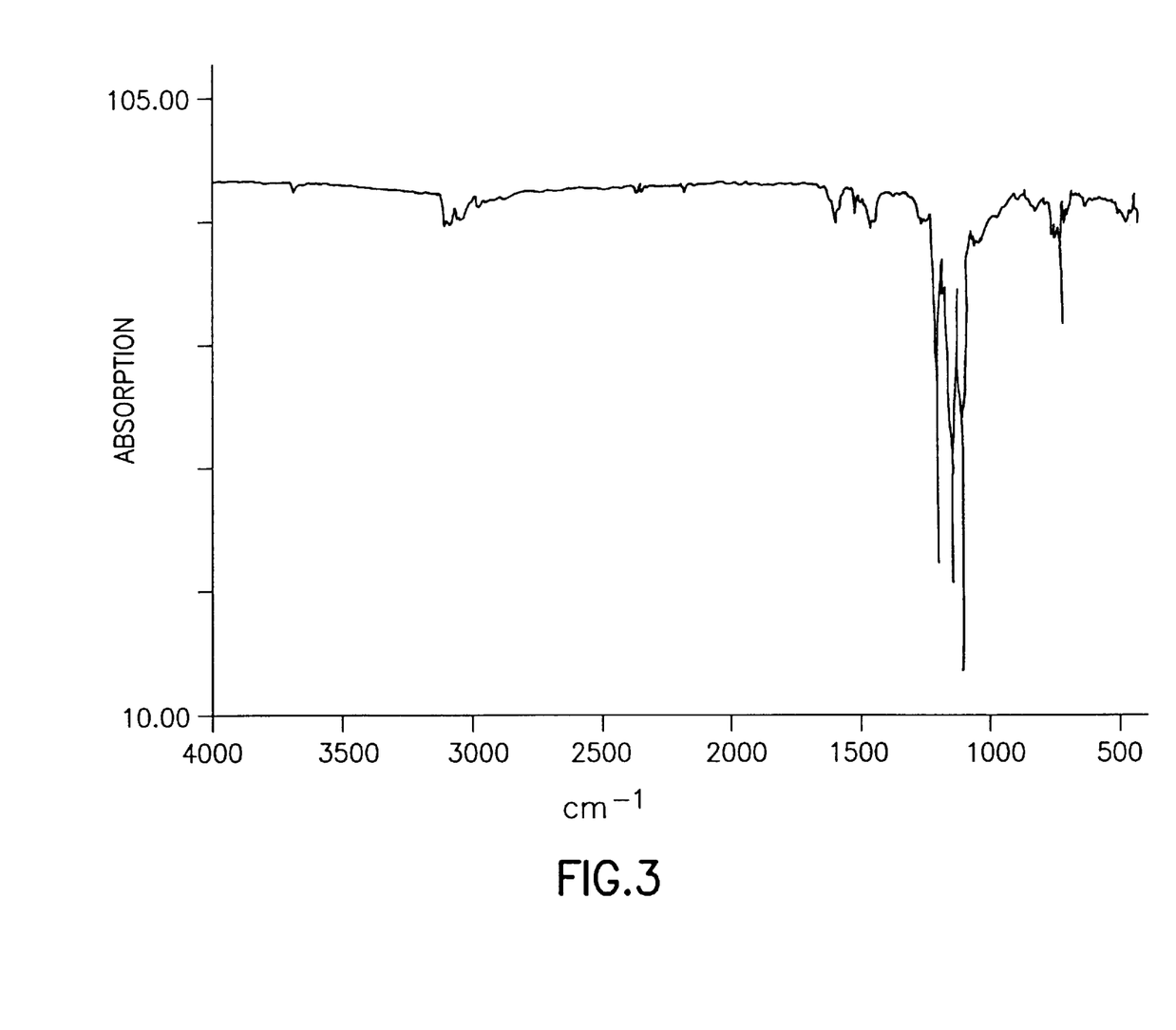
FIG. 3 shows a vapor phase FTIR spectrum of $(CF_3)_3SbNC_5H_5$ Lewis-base adduct, in which the presence of the C—H and C—C stretches indicate that pyridine is bound to the Sb, based upon spectral shifts and changes in relative intensity of the C—F bending and stretching modes.

In the FIG. 3 spectrum, the presence of the C—H and C—C stretches indicates that pyridine is present and bound to the Sb, based upon spectral shifts and changes in the relative intensity of the C—F bending and stretching modes.

The FTIR spectrum shows that there is a shift in the C—F modes, as well as the appearance of C—H stretching from the pyridine ring.

The $^{13}C$ NMR spectrum for $H_5C_5N{:}Sb(CF_3)_3$ shows a downfield shift of the carbon resonances relative to the pure compound. The shift is approximately 2.5 ppm, slightly less than that observed for the ammonia adduct (as expected, since ammonia is a stronger base than pyridine). The fact that the adduct bond is somewhat weaker in the pyridine molecule is indicative of the decomposition of the adduct at lower temperatures than the ammonia adduct.

Figure 4:
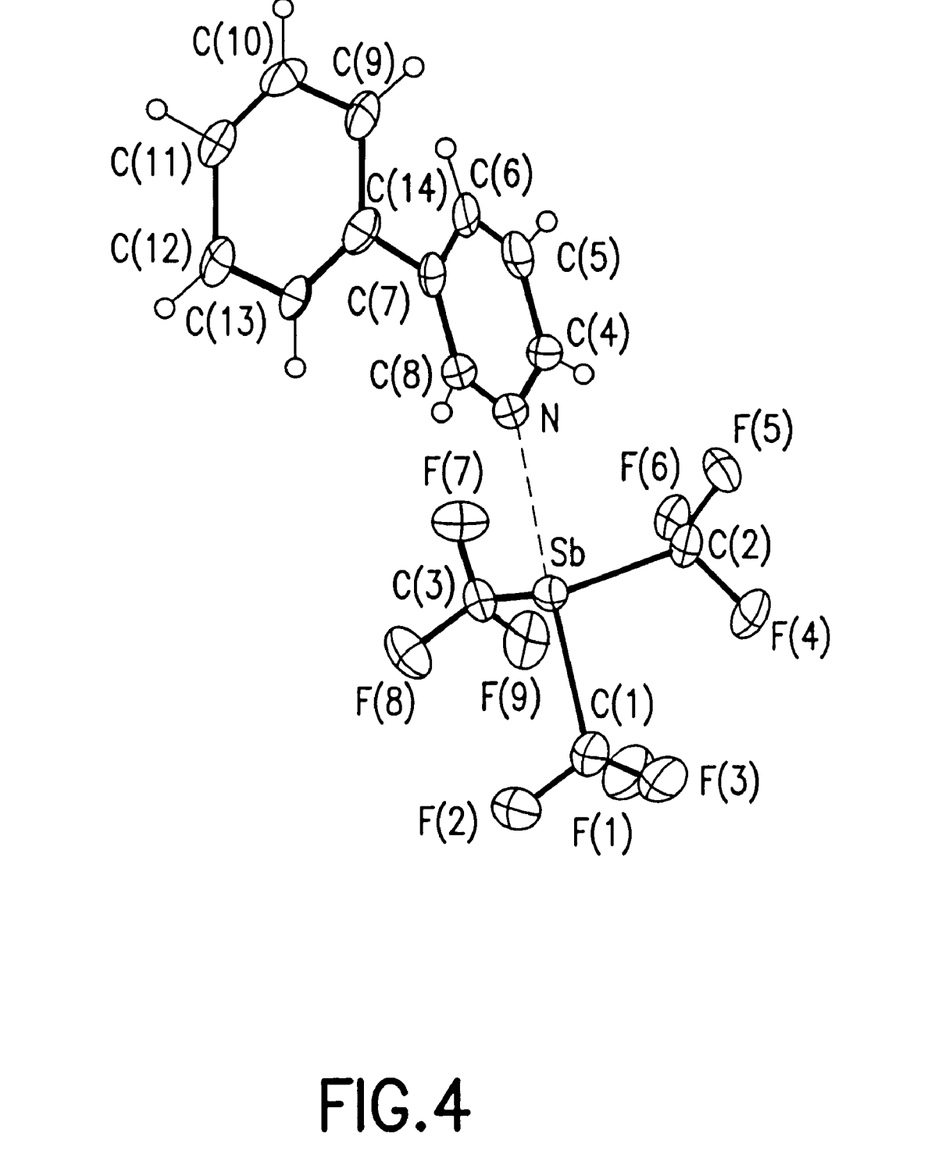
FIG. 4 is a schematic representation of the crystal structure of a 3-phenylpyridine tris-(trifluoromethyl)stibine adduct, showing that the Sb—N bond length is unexpectedly long, indicative of a very weak adduct bond.

The crystal structure of the other adduct, tris(trifluoromethylstibine)-3-phenylpyridine, is shown in FIG. 4 and displays a very interesting packing sequence. Of particular interest is the length of the Sb—N bond, which is exceptionally long. This unexpectedly long bond length indicates that the adduct is only very weakly bound, consistent with low temperature thermal decomposition in use of the adduct, so that the adduct provides a source of pure Sb for low temperature deposition applications, e.g., in chemical vapor deposition. Some applications including ion implant may suitably involve the provision of a polymer support with suitable donor groups that bind $Sb(CF_3)_3$ weakly (as shown in the crystal structure). This may provide a storage and delivery method.

The adducts of the invention have broad use as antimony sources for the CVD of antimonides and in the ion implantation of $Sb^+$ in the semiconductor industry, e.g., for the fabrication of III–V compound semiconductors, and for forming thin-film, long wavelength infrared detecting materials such as InSb, InAsSb, InGaSb, InSbBi and InAsSbBi.

Additionally, the antimony source reagents of the invention may be utilized to form InSb as an advantageous material for high speed devices due to its high electron mobility and maximum electron drift velocity. The growth of high-quality InSb epitaxial layers may be carried out with antimony sources of the present invention that decompose cleanly at low processing temperatures and thereby limit diffusion and melting of InSb (melting point=525° C.). In this respect, the adducts of the invention achieve a substantial advance in the art over traditional alkyl-antimony precursors. Such traditional precursors are not useful for the growth of high quality, crystalline InSb epitaxial layers which possess abrupt interfaces, because of the high processing temperatures ($\geq 460°$ C.) required for such traditional source reagents.

Adducts of the invention may be employed as precursors for depositing antimony in the fabrication of long wavelength (8–12 µm) infrared detector devices based upon InSbBi and InAsSbBi, as competitors to traditional, but more difficult to process, HgCdTe materials-based devices.

Adducts of the invention may be employed as precursors for depositing antimony in the fabrication of other devices, e.g., infrared optoelectronic devices such as Type-II quantum well lasers based on superlattice LED heterostructures (with quantum well structures comprised of materials such as InAsSb with cladding layers of InPSb and AlAsSb) to provide mid-infrared range emissions, chemical sensor systems, infrared military counter-measure devices, mid-infrared lasers involving active regions comprised of InAs/InGaSb/InAs with lattice matching to AlSb cladding layers, $InSb/In_{1-x}Al_xSb$ based light emitting diodes operating in the 4 µm to 7 µm range at room temperature, and devices for the detection of methane and carbon dioxide (with antimonide materials providing emission at wavelengths critical for the detection of methane (3.3 µm) and carbon dioxide (4.2 µm).

The antimony source reagents of the present invention may be provided in a preferred form as a sorbate which is sorptively retained on a suitable sorbent medium in a storage and dispensing vessel holding the physical sorbent and the antimony source reagent material, in accordance with the disclosure of U.S. Pat. No. 5,518,528 issued May 21, 1996 in the names of Glenn M. Tom and James V. McManus. The storage and dispensing vessel is equipped with suitable dispensing means such as a conventional valve head assembly, to provide on-demand dispensing of the storage antimony source gas. Such storage approach enables the adducts of the invention to constitute a reliable antimony source for commercialization.

Figure 5:
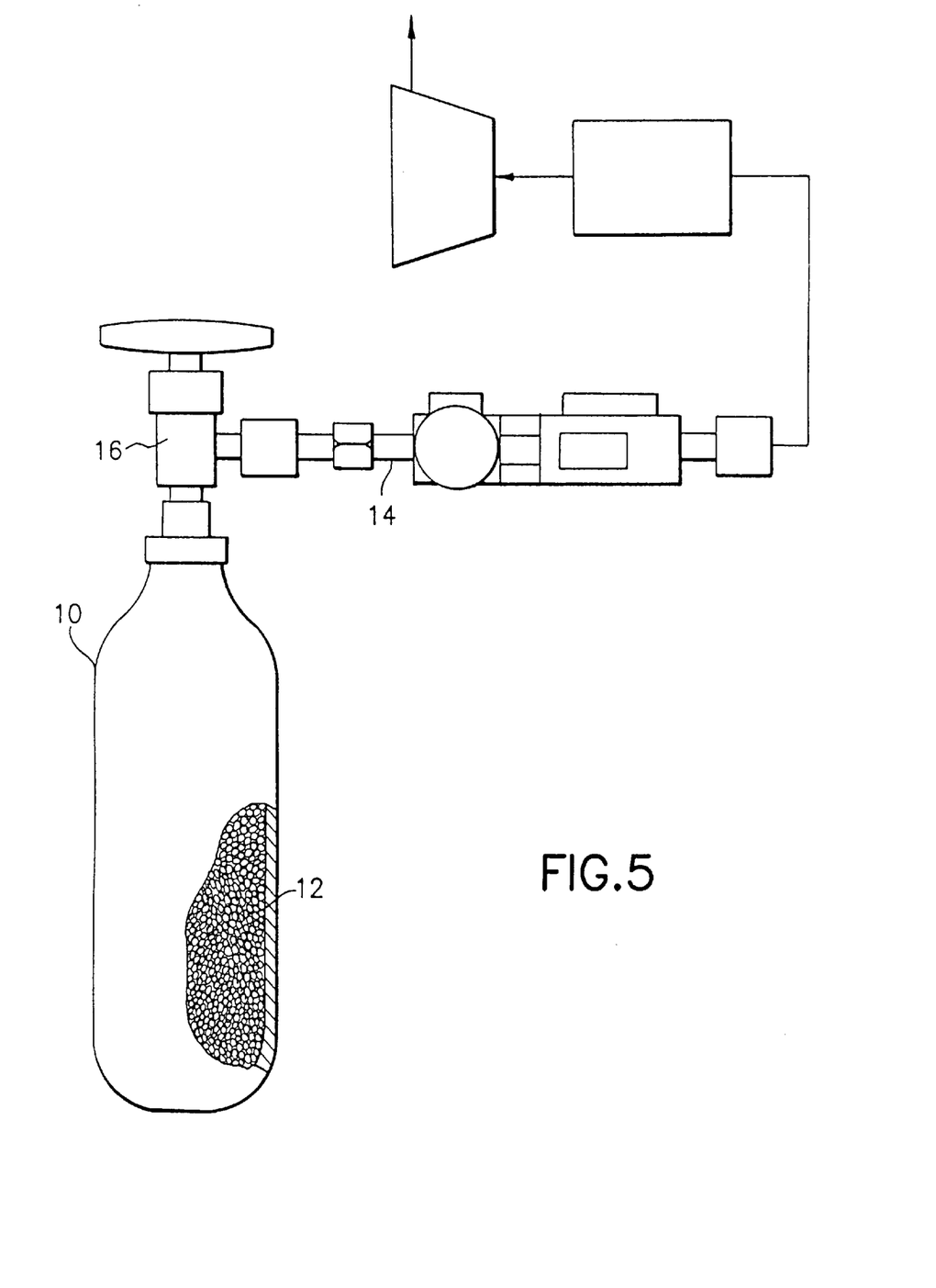
FIG. 5 is a schematic representation of a gas storage and dispensing vessel holding a sorbent medium and an antimony source reagent according to the invention.

FIG. 5 is a schematic representation of a gas storage and dispensing vessel 10 holding a sorbent medium 12 and a sorbate antimony adduct according to the invention. The gas storage and dispensing vessel may be constructed and arranged as more fully described in the aforementioned Tom et al. patent, and features a dispensing manifold 14 joined to the valve head 16 of the vessel as illustrated. By the apparatus shown in FIG. 5, the antimony adduct source reagents of the present invention may be stored for extended periods of time, and supplied on demand for such applications as ion implantation and chemical vapor deposition.

The adducts of the present invention may optionally in some applications be derivatized to the extent of any hydrogen substituent(s) on the antimony nuclear atom, by replacing one or more of such hydrogen substituent(s) with deuterium ($^2_1H$) or tritium ($^3_1H$) isotope, as more fully described in our co-filed U.S. patent application Ser. No. 08/977,225 filed Nov. 24, 1997 in the names of Michael A. Todd, Thomas H. Baum and Gautam Bhandari for "Stable Hydride Source Compositions for Manufacture of Semiconductor Devices and Structures," the disclosure of which is hereby incorporated herein by reference in its entirety. Such derivatization may be desired for further enhancing the stability of the adducts of the present invention.

Further, while the invention has been described herein with specific and primary reference to antimony as the metal species of interest in the adducts of the present invention, the invention is not thus limited, and may find application in other metal source compositions, e.g., with metals such as aluminum, gallium, tin, germanium, indium, etc., or other Group III, IV or V metal or a transition metal, in place of antimony.

The features and advantages of the invention are more fully shown by the following non-limiting Examples. In these Examples the experimental procedures were as follows:

Experimental Procedures

General Procedures

All synthetic work was performed in a nitrogen filled glovebox (Vacuum Atmospheres Model HE-553-4) or under dry nitrogen using standard vacuum line and Schlenk techniques. Unless noted otherwise, all chemicals were used as received from the vendor. The FTIR spectra were collected on a Perkin Elmer model 1650 spectrometer. Nuclear magnetic resonance spectra were recorded on a Varian Gemini 200 MHz spectrometer. Differential Scanning Calorimetry/Scanning Thermal Analysis (DSC/TGA) was performed on a Rheometric Scientific model STA 1000 apparatus. Crystal structures were determined using a diffractometer.

Thin Film Deposition

The thin films described in this work were deposited in a horizontal, resistively heated, hot-walled 1.5" CVD reactor. Temperature control was accomplished using a Eurotherm model 847 temperature controller and reactant and carrier gases were introduced via mass flow controllers. Pumping of the reactor system was accomplished using a liquid nitrogen trapped diffusion pump and resulted in a base pressure approaching $10^{-6}$ Torr. Processing pressures were monitored via a baratron capacitance manometer gauge and varied by changing the reactant and carrier gas flow rates. The condensible decomposition byproducts were collected in a glass trap cooled to liquid nitrogen temperature and were analyzed using FTIR and, when possible, NMR. Analysis of these byproducts in conjunction with analysis of the film properties and compositions allowed for optimization of the processing conditions.

Tris(trifluoromethyl)stibine, $Sb(CF_3)_3$, was synthesized via reaction in a high-pressure stainless steel autoclave. Lewis base adducts of tris(trifluoromethyl)stibine containing ammonia, pyridine, 3-phenyl-pyridine and 3-picoline were also synthesized and found to be suitable precursors for antimonide CVD.

The thermal decomposition of these molecules was examined using a hot-walled CVD reactor system and low temperature CVD of antimony was demonstrated, thereby evidencing that the Sb adducts of the invention exhibit vast potential for antimonide film growth and low temperature CVD applications.

EXAMPLE I

Precursor Syntheses

Tris(trifluoromethyl)stibine, $Sb(CF_3)_3$, denoted hereafter as compound 1, was prepared at 175° C. and 40 atm in a 90 ml stainless steel Parr autoclave by reacting antimony metal with trifluoromethyl iodide. The pure compound was isolated from iodobis(trifluoromethyl)stibine and diiodotrifluoromethylstibine, via trap-trap vacuum distillation, in 35% yield. $Sb(CF_3)_3$ is a colorless, mobile liquid (mp.−58° C.) with a room temperature vapor pressure of 81 Torr. It is thermally stable up to 200° C., but reacts explosively on exposure to oxygen, and was handled accordingly. These physical properties greatly limit the utility of compound 1 for CVD applications.

Compound 1 was characterized by comparison of $^{13}C$ NMR spectra with the chemical shifts reported in the literature and by vapor phase FTIR spectroscopy.

Compound 1, $Sb(CF_3)_3$ was utilized in the synthesis of Lewis acid-base adducts with pyridine, 3-phenylpyridine, ammonia and 3-picoline. These were prepared by condensing $Sb(CF_3)_3$ at −196° C. into a reaction vessel containing the appropriate Lewis base. The pyridine adduct, compound 2, is a colorless solid (mp. 40–41° C.) with a room temperature vapor pressure of approximately 2 Torr while the 3-phenylpyridine adduct, compound 3, is a colorless solid with a room temperature vapor pressure below one Torr. The simultaneous thermogravimetric analysis and differential scanning calorimetry (TGA/DSC) data for compound 2 reveal that the adduct melts and sublimes cleanly. These properties, combined with a marked decrease in reactivity towards oxygen exposure, make compound 2 highly useful as a CVD precursor. Crystallographic data was collected from crystals of 3, and showed that its structure of the crystals was highly symmetrical in nature.

The ammonia and 3-picoline adducts, compounds 4 and 5, respectively, are both mobile colorless liquids at room temperature. Compound 4 displays a room temperature vapor pressure of 31 Torr and is much less reactive towards oxygen than the parent compound (merely fuming on exposure to oxygen, rather than exploding). These properties, coupled with the lack of carbon atoms in the adduct ligand make compound 4 a useful and desirable CVD source.

The vapor phase FTIR spectrum of compound 4 revealed strong C—F stretching modes at 1190–1127 $cm^{-1}$ and the characteristic $-CF_3$ deformation mode at 722 $cm^{-1}$, as well as the N—H stretch at 3033 $cm^{-1}$. The decrease in the symmetry of the adduct relative to the free molecules is readily observed by the lack of the p and r branches in the ammonia-related stretching and bending modes (3033 and 1374 $cm^{-1}$), which was compared with the spectrum of the small amount of unbound ammonia added to the sample (N—H stretching at 3331 $cm^{-1}$) for reference purposes.

In all cases, the observed chemical shifts of trifluoromethyl carbon atoms in spectra of the adduct species are downfield relative to those observed for pure $Sb(CF_3)_3$.

EXAMPLE II

Film Deposition

Compound 1 was thermally decomposed in a horizontal, hot-walled, low-pressure CVD reactor at temperatures as low as 275° C. to yield thin films of antimony. Most depositions, however, were carried out at 350–400° C. due to low growth rates below 350° C.

The precursor was introduced pure and in diluted mixtures of compound 1 and $H_2$. Typical growth times were thirty minutes to one hour and resulted in thick films of antimony. Films were deposited on Si, Pt/Si, glass (Pyrex) and $SiO_2$. Good adherence was observed on Pyrex glass and Pt/Si, but poor adherence was observed on Si and $SiO_2$. In addition, thick films deposited on Pt/Si were observed to have pinholes.

Observation of the film surfaces by SEM and AFM analyses revealed that thick films of antimony deposited on platinum coated (100) Si at 350° C. have rough surfaces and are polycrystalline. A typical image obtained from an antimony-containing film deposited at 400° C. using compound 2 showed a rough surface obtained from deposition on platinum coated (100) Si, which resulted in the formation of Geversite, a platinum-antimony alloy of composition $PtSb_2$.

The decomposition byproducts for many depositions were collected in a liquid nitrogen cold trap and later examined using FTIR spectroscopy. The main components of the volatile byproducts were identified as tetrafluoroethylene, hexafluoroethane and unreacted starting material. A white solid residue was also observed in the reactor tube outside the hot zone. An FTIR analysis of the material revealed that it possessed strong C—F stretches at 1165–1050 $cm^{-1}$, suggesting that it may have been a mixture of C—F polymers formed by recombination of $CF_3$ and $CF_2$ radicals produced during the decomposition.

The decomposition of compounds 2 and 4 was carried out in the same reactor system at temperatures as low as 330° C. and 300° C., respectively, to yield thin films of antimony on Si, Pt/Si, glass (Pyrex) and $SiO_2$ substrates. Based upon film growth rate and analysis of the decomposition byproducts, a suitable deposition temperature for pure Sb films from the ammonia adduct of compound 1 was determined as 375° C. Pure antimony films were obtained from compound 4 at deposition temperatures above 400° C.

EXAMPLE III
Film Composition

The composition and purity of the films deposited were investigated using x-ray diffraction (XRD), energy dispersive x-ray analysis (EDS) and Fourier transform infrared spectroscopy (FTIR) (of films deposited on (100) Si). A typical XRD pattern of a antimony film deposited on platinum coated (100) Si at 400° C. using compound 4 revealed a number of x-ray peaks which correspond to Geversite, $PtSb_2$, an alloy of platinum and antimony which forms during the thermal decomposition of all of the molecules investigated. No peaks corresponding to antimony oxide phases were observed, nor was any oxygen or carbon observed via EDS or FTIR analyses.

EXAMPLE IV
Synthesis of $Sb(CF_3)_3$ (1)

A stainless steel autoclave (90 ml volume) was thoroughly dried under vacuum and then charged with antimony metal (20 g, 164 mmol) in a nitrogen-filled glove box. The bomb was then attached to a high vacuum manifold and evacuated to insure that its seals were leak tight. Trifluoriodomethane (35.2 g, 180 mmol) was condensed into the auto-clave at −196° C. and the bomb was allowed to warm to room temperature. The autoclave was then immersed in a high temperature oil bath which was heated to 175° C. (monitored via a thermocouple temperature gauge) for a period of 24–36 hours at a maximum pressure approaching 40 atmospheres. The bomb was manually agitated during this process to insure adequate mixing of the reagents. During the course of the reaction the pressure was noted to steadily decrease (indicating the consumption of $CF_3I$ and the formation of $Sb(CF_3)_3$) until it reached a value of approximately 10 atm. The bomb was allowed to cool and then attached to a high vacuum manifold via stainless steel bellows tubing. The volatile products were then passed through traps held at −25° C., −70° C. and −196° C. in order to isolate $Sb(CF_3)_3$ in the −70° C. trap. The −196° C. trap was found to contain unreacted $CF_3I$ and and a small amount of a mixture of fluorocarbon gases (eg. $C_2F_6$), while the −20° C. trap was found to contain a small amount of highly unstable $I_2SbCF_3$ and $ISb(CF_3)_2$, both of which rapidly decomposed during room temperature storage. The autoclave was found to contain a red-orage solid, which, based on its melting point, was determined to be a mixture of $SbI_3$ and Sb (m). A typical reaction resulted in the isolation of $Sb(CF_3)_3$ (3.5 g, 11 mmol) in approximately 35% yield (based upon the amount of $CF_3I$ consumed during the reaction).

Tris(trifluormethyl)stibine is a colorless, mobile liquid (mp. −58° C.) with a vapor pressure of 81 Torr at room temperature. It reacts explosively on contact with oxygen and was handled with great care. $Sb(CF_3)_3$ was characterized using vapor phase FTIR, mass spectrometry (via ion implantation testing) and NMR, as well as by crystal structure determination of the phenylpyridine adduct. Vapor Phase FTIR: 2379 cm$^{-1}$ (vw), 2276 cm$^{-1}$ (vw), 2219 cm$^{-1}$ (vw), 2180 cm$^{-1}$ (w), 1326 cm$^{-1}$ (vw), 1274 cm$^-$(w), 1242cm$^{-1}$ (w), 1190 cm$^{-1}$ (vs), 1146 cm$^{-1}$ (vs), 1127 cm$^{-1}$ (vs), 1092 cm$^{-1}$ (vs), 1069 cm$^{-1}$ (sh), 1042 cm$^{-1}$ (w), 990 cm$^{-1}$ (vw), 867 cm$^{-1}$ (vw), 723 cm$^{-1}$ (m), 517 cm$^{-1}$ (vw).

$^{13}C$ NMR (referenced to $C_6D_6$): 143.9, 136.7, 129.5, and 122.3 ppm (q, CF3).

$^{13}C$ NMR (referenced to $CDCl_3$): 143.2 ppm, 136.0, 128.9 and 121.7 ppm (q, CF3).

EXAMPLE V
Synthesis of $Sb(CF_3)_3$—$NH_3$ Lewis Base Adduct (2) Into a 25 ml flask charged with $Sb(CF_3)_3$ (0.5 g, 1.52 mmol), pre-dried ammonia (0.026 g, 1.52 mmol) was condensed at −196° C.

The resulting mixture was allowed to slowly warm to room temperature. The resulting solution was stirred un-der vacuum for 1 hour using a teflon stirbar. During the synthesis of this adduct, it was discovered that an excess of $Sb(CF_3)_3$ results in the formation of a yellowish, non-volatile solid, while the use of excess ammonia merely leads to the formation of the mono-substituted adduct. A typical synthesis results in nearly quantitative yields of $H_3N:Sb(CF_3)_3$ (0.52 g, 1.5 mmol).

$H_3N:Sb(CF_3)_3$ is a mobile liquid with a room temperature vapor pressure of 31 Torr. The molecule exhibits remarkably reduced reactivity towards air relative to $Sb(CF_3)_3$, merely fuming on exposure, rather than igniting.

Gas Phase FTIR: 3053 cm$^{-1}$ (w), 3040 cm$^{-1}$ (m, sh), 3033 cm$^{-1}$ (m), 3015 cm$^{-1}$ (w), 2285 cm$^{-1}$ (vw), 2182 cm$^{-1}$ (vw), 1374 cm$^{-1}$ (s), 1227 cm$^{-1}$ (w), 1207 cm$^{-1}$ (m,sh), 1190 cm$^{-1}$ (vs, sh), 1149 cm$^{-1}$ (vs), 1127 cm$^{-1}$ (vs), 1092 cm$^{-1}$ (w, sh), 1068 cm$^{-1}$ (m,sh), 1063 cm$^{-1}$ (m, sh), 1029 cm$^{-1}$ (vw), 964 cm$^{-1}$ (w), 930 cm$^{-1}$ (w), 739 cm$^{1}$ (vw), 722 cm$^{-1}$ (m), 699 cm$^{-1}$ (m), 523 cm$^{-1}$ (vw), 506 cm$^{-1}$ (w).

$^1$ H NMR (Referenced to $CDCl_3$): 1.43 ppm (s, $NH_3$).

$^{13}C$ NMR (Referenced to $CDCl_3$): 145.7 ppm, 138.4 ppm, 131.2 ppm, 124.0 ppm (q, $Sb(CF_3)_3$).

EXAMPLE VI
Synthesis of $Sb(CF_3)_3$—$NC_5H_5$ Lewis Base Adduct (3)

A flask was charged with anhydrous pyridine (0.12 g, 1.52 mmol) in a nitrogen filled glove box and then degassed at −196° C. $Sb(CF_3)_3$ (0.5 g, 1.52 mmol) was condensed into the flask which was allowed to slowly warm to room temperature. The adduct was observed to form immediately upon warming. $H_5C_5N:Sb(CF_3)_3$ (mp. 40–41° C.) was collected in quantitative yield as a pure white, low melting solid via vacuum distillation. This Lewis base adduct displays an amazing room temperature vapor pressure of nearly 2 Torr and transports readily under reduced pressures without heating.

$H_5C_5N:Sb(CF_3)_3$ is a volatile white solid which displays a much higher degree of stability than the parent molecule, $Sb(CF_3)_3$, with respect to air reactivity. The pyridine adduct fumes on contact with air, but does not ignite explosively.

Vapor Phase FTIR: 3692 cm$^{-1}$ (vw), 3092 cm$^{-1}$ (w), 3085 cm$^{-1}$ (w), 3039 cm$^{-1}$ (w), 2966 cm$^{-1}$ (vw), 2177 cm$^{-1}$ (vw), 1585 cm$^{-1}$ (vw), 1506 cm$^{-1}$ (vw), 1447 cm$^{-1}$ (w), 1252 cm$^{-1}$ (w), 1190 cm$^{-1}$ (vs), 1148 cm$^{-1}$ (s), 1128 cm$^{-1}$ (vs), 1092 cm$^{-1}$ (vs), 1072 cm$^{-1}$ (m,sh), 1042 cm$^{-1}$ (w), 1015 cm$^{-1}$ (w), 952 cm$^{-1}$ (vw), 867 cm$^{-1}$ (vw), 795 cm$^{-1}$ (w), 734 cm$^{-1}$ (m), 711 cm$^{-1}$ (m), 685 cm$^{-1}$ (vw), 607 cm$^{-1}$ (vw), 515 cm$^{-1}$ (w).

$^1$H NMR (Referenced to $C_6D_6$): 8.30 (1 ppm coupling constant) ppm (doublet), 6.97 ppm (4 ppm coupling constant) (t), 6.64 (2 ppm coupling constant) ppm (t).

$^{13}C$ NMR (referenced to $C_6D_6$): I) $Sb(CF_3)_3$: 146.5 ppm, 139.3 ppm, 132.0 ppm, 125.9 ppm II) $NC_5H_5$: 149.1 ppm, 136.3 ppm, 124.0 ppm.

EXAMPLE VII
Synthesis of $Sb(CF_3)_3$—$NC_5H_4$ ($C_6H_5$) Lewis Base Adduct (4)

A flask was charged with 3-phenylpyridine (0.24 g, 1.52 mmol) in a nitrogen filled glove box and then degassed at −196 ° C. $Sb(CF_3)_3$ (0.5 g, 1.52 mmol) was condensed into the flask using liquid nitrogen. The mixture was allowed to slowly warm to room temperature, at which point it was observed that it had formed a brownish oily solid. Recrystallization from pentane afforded $Sb(CF_3)_3$—$NC_5H_4(C_6H_5)$ (0.3 g, 62 mmol, 40%) as low melting crystals.

$Sb(CF_3)_3$—$NC_5H_4(C_6H_5)$ is a viscous brownish oil which exhibits a vapor pressure of less than one Torr at room temperature. It is markedly less reactive towards oxygen than $Sb(CF_3)_3$.

Vapor Phase FTIR: 2968 cm$^{-1}$ (w), 2931 cm$^{-1}$ (w,sh), 2880 cm$^-$(vw), 2461 cm$^{-1}$ (vw), 1248 cm$^{-1}$ (w), 1190 cm$^{-1}$ (s), 1145 cm$^{-1}$ (m), 1125 cm$^{-1}$ (s), 1091 cm$^{-1}$ (vs), 1039 cm$^{-1}$ (vw), 721 cm$^{-1}$ (w).

$^1$H NMR (Referenced to CDCl$_3$): 8.83 ppm (s,), 8.57 ppm (d,), 7.91 ppm (d,), multiplet centered at 7.48 ppm, 0.1 ppm (s,).

$^{13}$C NMR (Referenced to CDCl$_3$): I) phenylpyridine portion of molecule: 147.9 ppm, 137.5 ppm, 134.8 ppm, 129.1 ppm, 128.2 ppm, 127.1 ppm, 123.8 ppm, 1.0 ppm II) $Sb(CF_3)_3$ portion of molecule: 145.1 ppm, 137.8 ppm, 130.6 ppm, ~123 ppm (hidden beneath phenylpyridine signal).

EXAMPLE VIII

Synthesis of $Sb(CF_3)_3$—3-picoline Lewis Base Adduct (5)

Neat 3-picoline, $NC_5H_4(CH_3)$, (0.15 g, 1.52 mmol) was placed in a flask in a nitrogen filled golve box and later degassed at -196° C. $Sb(CF_3)_3$ (0.5 g, 1.52 mmol) was subsequently condensed into the flask, which was allowed to warm to room temperature. After stirring the mixture at room temperature for one-half hour, the liquid products were filtered under nitrogen to yield $Sb(CF_3)_3$:3-picoline (0.6 g, 1.4 mmol, 93%) as a mobile liquid.

Liquid (neat) FTIR: 3039 cm$^{-1}$ (m), 3000 cm$^{-1}$ (m), 2962 cm$^{-1}$ (m), 2923 cm$^{-1}$ (m), 2862 cm$^{-1}$ $^{(m)}$, 2746 cm$^{-1}$ (vw), 2615 cm$^{-1}$ (vw), 2477 cm$^{-1}$ (vw), 2185 cm$^{-1}$ (w), 1969 cm$^{-1}$ (vw), 1923 cm$^{-1}$ (vw), 1908 cm$^{-1}$ (vw), 1869 cm$^{-1}$ (vw), 1839 cm$^{-1}$ (vw), 1731 cm$^{-1}$ (vw), 1600 cm$^{-1}$ (m), 1583 cm$^{-1}$ (m), 1480 cm$^-$(s), 1453 cm$^{-1}$ (m), 1419 cm$^{-1}$ (m) 1388 cm$^{-1}$ (w), 1236 cm$^{-1}$ (m,sh), 1220 cm$^{-1}$ (s,sh), 1162 cm$^{-1}$ (vs), 1115 cm$^{-1}$ (vs), 1077 cm$^{-1}$ (vs), 1036 cm$^{-1}$ (vs), 988 cm$^{-1}$ (w, sh), 944 cm$^{-1}$ (vw), 920 cm$^{-1}$ (vw), 790 cm$^{-1}$ (s), 718 cm$^{-1}$ (s), 704 cm$^{-1}$ (s), 636 cm$^{-1}$ (m), 537 cm$^{-1}$ (w,sh), 513 cm$^{-1}$ (w), 462 cm$^{-1}$ (w).

$^1$H NMR (Referenced to CDCl$_3$, values in parentheses are for pure 3-picoline in CDCl$_3$): 8.37 ppm (s,) (8.03), 7.63 ppm (d,) (7.04, 7.01), 7.29 ppm (q,) (6.76, 6.73, 6.72, 6.70), 2.38 ppm (s,) (1.87).

$^{13}$C NMR (Referenced to CDCl$_3$, values in parentheses are for pure 3-picoline in CDCl$_3$): 148.6 ppm (149.4), 145.4 ppm (146.1), 138.2 ppm (135.4), 134.5 ppm (132.1), 130.8 ppm, 124.1 ppm (122.2), 18.5 ppm (17.4).

While the invention has been illustratively described herein with reference to specific features, aspects and embodiments, it will be appreciated that the invention is not thus limited, but rather extends to and encompasses numerous variations, modifications and other embodiments. The invention therefore is to be correspondingly broadly construed consistent with the claims hereinafter set forth.

What is claimed is:

1. An antimony/Lewis base adduct of the formula:

$SbR_3 \cdot L$ wherein:
each R substituent is independently selected from halo, deuterium, tritium, $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, and substituted $C_6$–$C_{10}$ aryl; and L is a Lewis base ligand coordinating with $SbR_3$, wherein L comprises a Lewis base ligand selected from the group consisting of:
(a) polyamines;
(b) pyridines;
(c) bipyridines;
(d) phenylpyridines;
(e) ammonia;
(f) crown ethers; and
(g) ligands of the formula: $R^0O(C(R^1)_2C(R^2)_2O)_nR^0$ wherein:
$R^0$=H, methyl, ethyl, n-propyl, cyanato, perfluoroethyl, perfluoro-n-propyl, or vinyl;
$R^1$=H,F, or a sterically acceptable hydrocarbyl substituent;
$R^2$=H,F, or a sterically acceptable hydrocarbyl substituent;
n=2,3,4,5, or 6; and
each $R^0$, $R^1$, and $R^2$ may be the same as or different from the other $R^0$, $R^1$, and $R^2$, respectively.

2. An antimony/Lewis base adduct according to claim 1, wherein L comprises a Lewis base ligand selected from the group consisting of tetraglyme, bipyridine, ammonia, pyridine, 3-phenylpyridine, 18-crown6 ether, pentamethyldiethylenetriamine (PMDETA), diethylenetriamine (DETA), tetraethylenepentaamine (TEPA) and hexamethyltetraethylenepentaamine (HMTEPA).

3. A tris(trifluoromethyl)stibine adduct of the formula:

$Sb(CF_3)_3 \cdot L$ wherein L is a Lewis base ligand coordinating with $Sb(CF_3)_3$, wherein L comprises a Lewis base ligand selected from the group consisting of:
(a) amines and polyamines;
(b) pyridines;
(c) bipyridines;
(d) phenylpyridines;
(e) ammonia;
(f) crown ethers; and
(g) ligands of the formula: $R^0O(C(R^1)_2C(R^2)_2O_nR^0$ wherein:
$R^0$=H, methyl, ethyl, n-propyl, cyanato, perfluoroethyl, perfluoro-n-propyl, or vinyl;
$R^1$=H,F, or a sterically acceptable hydrocarbyl substituent;
$R^2$=H,F, or a sterically acceptable hydrocarbyl substituent;
n=2,3,4,5, or 6; and
each $R^0$, $R^1$, and $R^2$ may be the same as or different from the other $R^0$, $R^1$, and $R^2$, respectively.

4. An antimony/Lewis base adduct according to claim 3, wherein L comprises a Lewis base ligand selected from the group consisting of:
(a) amines and polyamines;
(b) bipyridines;
(c) crown ethers; and
(d) ligands of the formula: $R^0O(C(R^1)_2C(R^2)_2O)_nR^0$ wherein:
$R^0$=H, methyl, ethyl, n-propyl, cyanato, perfluoroethyl, perfluoro-n-propyl, or vinyl;
$R^1$=H,F, or a sterically acceptable hydrocarbyl substituent;
$R^2$=H,F, or a sterically acceptable hydrocarbyl substituent;

n=2,3,4,5, or 6; and each $R^0$, $R^1$, and $R^2$ may be the same as or different from the other $R^0$, $R^1$, and $R^2$, respectively.

5. An antimony/Lewis base adduct according to claim 4, wherein L comprises a Lewis base ligand selected from the group consisting of tetraglyme, bipyridine, ammonia, pyridine, 3-phenylpyridine, 18-crown-6 ether, pentamethyldiethylenetriamine (PMDETA), diethylenetriamine (DETA), tetraethylenepentaamine (TEPA) and hexamethyltetraethylenepentaamine (HMTEPA).

6. An antimony/Lewis base adduct of the formula $SbR_3.L$, wherein at least one R substituent of $SbR_3$ is a deuterium ($^2_1H$) isotope or a tritium ($^3_1H$) isotope, and L is selected from the group consisting of:

(g) amines and polyamines;
(h) pyridines;
(i) bipyridines;
(j) phenylpyridines;
(k) ammonia;
(f) ligands of the formula:

wherein:
G is —O—, —S—, or —NR—, wherein R is H or hydrocarbyl,
(g) crown ethers;
(h) thioethers; and
(i) ligands of the formula: $R^0O(C(R^1)_2C(R^2)_2O)_nR^0$
wherein:
$R^0$=H, methyl ethyl, n-propyl, cyanato, perfluoroethyl, perfluoro-n-propyl, or vinyl,
$R^1$=H,F, or a sterically acceptable hydrocarbyl substituent;
$R^2$=H,F, or a sterically acceptable hydrocarbyl substituent;
n=2,3,4,5, or 6; and
each $R^0$, $R^1$, and $R^2$ may be the same as or different from the other $R^0$, $R^1$, and $R^2$, respectively.

7. An antimony/Lewis base adduct of the formula $SbR_3.L$, wherein at least one R substituent of $SbR_3$ is a deuterium ($^2_1H$) isotope, and L is selected from the group consisting of:

(l) amines and polyamines;
(m) pyridines;
(n) bipyridines;
(o) phenylpyridines;
(p) ammonia;
(f) ligands of the formula:

wherein:
G is —O—, —S—, or —NR—, wherein R is H or hydrocarbyl,
(g) crown ethers;
(h) thioethers; and
(i) ligands of the formula: $R^0O(C(R^1)_2C(R^2)_2O)_nR^0$
wherein:

$R^0$=H, methyl, ethyl, n-propyl, cyanato, perfluoroethyl, perfluoro-n-propyl, or vinyl,
$R^1$=H,F, or a sterically acceptable hydrocarbyl substituent;
$R^2$=H,F, or a sterically acceptable hydrocarbyl substituent;
n=2,3,4,5, or 6;and
each $R^0$, $R^1$, and $R^2$ may be the same as or different from the other $R^0$, $R^1$, and $R^2$, respectively.

8. An adduct according to claim 1, comprising an adduct of $Sb(CF_3)_3$ with one of ammonia, pyridine and phenylpyridine.

9. An adduct according to claim 1, comprising $H_3N:Sb(CF_3)_3$.

10. An adduct according to claim 1, comprising $H_5C_5N:Sb(CF_3)_3$.

11. An adduct according to claim 1, comprising $(H_5C_6)H_4C_5N:Sb(CF_3)_3$.

12. An adduct according to claim 1, comprising $(H_3C)H_4C_5N:Sb(CF_3)_3$.

13. An antimony adduct of the formula:

$$SbR_3.L$$

wherein:
each R substituent is independently selected from halo, deuterium, tritium, $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, and substituted $C_6$–$C_{10}$ aryl; and
L is a ligand coordinating with $SbR_3$ and selected from the group consisting of: ammonia;
polyamines;
pyridine;
bipyridines;
ethers;
tetraglyme; and
thioethers subject to the provisos that: when all of said R substituents are butyl, L is not tetrahydrofuran, and when all of said R are trifluoromethyl, L is not furan, thiophene, or pyrrole.

14. An antimony adduct of the formula:

$$SbR_3.L$$

wherein:
each R substituent is independently selected from halo, deuterium, tritium, $C_1$–$C_8$ alkyl, $C_1$–$C_8$ perfluoroalkyl, $C_1$–$C_8$ haloalkyl, $C_6$–$C_{10}$ aryl, $C_6$–$C_{10}$ perfluoroaryl, $C_6$–$C_{10}$ haloaryl, $C_6$–$C_{10}$ cycloalkyl, and substituted $C_6$–$C_{10}$ aryl; and
L is a ligand coordinating with $SbR_3$ and selected from the group consisting of:
ammonia;
polyamines;
pyridine;
bipyridines;
phenylpyridine;
picoline; and
tetraglyme.

15. An antimony adduct according to claim 14, wherein each of the R substituents is trifluoromethyl.

16. An antimony adduct of the formula:

$$SbR_3.L$$

wherein:
each R substituent is independently selected from deuterium, tritium, and $C_1$–$C_8$ perfluoroalkyl; and L is a ligand coordinating with SbR$_3$ and selected from the group consisting of:
ammonia;
pyridine;
phenylpyridine;
picoline;
tetrahydrofuran;
tetraglyme;
bypyridine;
crown ethers;
pentamethyldiethylenetriamine;
diethylenetriamine;
tetraethylenepentaamine; and
hexamethyltetraethylenepentaamine.

17. An antimony adduct according to claim 16, wherein each R is trifluoromethyl.

18. Tris(trifluoromethylstibine)-3-phenylpyridine.

* * * * *

UNITED STATES PATENT AND TRADEMARK OFFICE
CERTIFICATE OF CORRECTION

PATENT NO.    : 6,005,127
DATED         : December 21, 1999
INVENTOR(S)   : Michael A. Todd; Thomas H. Baum; Gautam Bhandari It is certified that error appears in the above-identified patent and that said Letters Patent is hereby corrected as shown below:

Column 5,
Line 27: change "or6" to -- or 6 --.

Column 6,
Lines 8-12: add a space before "(I)", "(I)", and "(s)".

Column 9,
Line 1: change "vacuum line" to -- vacuum-line --.

Column 11:
Line 58: after "adduct." Start a new paragraph.
Line 60: change "1274 cm⁻(w)" to -- 1274 $cm^{-1}$(w) --.

Column 12:
Line 1: after (2) start a new paragraph.
Line 6: Do not start a new paragraph here.
Line 24: change 739 $cm^{1}$" to -- 739 $cm^{-1}$ --.
Line 61: change "$NC_sH_4$" to -- $NC_5H_5$ --.

Column 13,
Line 2:  change "$NC_sH_4$" to -- $NC_5H_5$ --.
Line 4:  change "$NC_sH_4$" to -- $NC_5H_5$ --.
Line 9:  change "2880 cm⁻(vw)," to -- 2880 $cm^{-1}$(vw) --.
Line 32: change "2862 $cm^{-1(m)}$," to -- 2880 $cm^{-1}$(vw) --.
Line 36: change 1480 cm⁻(s)" to -- 1480 $cm^{-1}$(m), --.
Line 60: change "$SbR_3$.L" to -- $SbR_3$•L --.

Column 14,
Line 24: change "18-crown6" to -- 18-crown-6 --.
Line 30: change "$Sb(CF_3)_3$.L" to -- $Sb(CF_3)_3$•L --.

UNITED STATES PATENT AND TRADEMARK OFFICE
CERTIFICATE OF CORRECTION

PATENT NO.    : 6,005,127
DATED         : December 21, 1999
INVENTOR(S)   : Michael A. Todd; Thomas H. Baum; Gautam Bhandari Page 2 of 2

It is certified that error appears in the above-identified patent and that said Letters Patent is hereby corrected as shown below:

Column 15,
Line 4: change "4" to -- 3--.
Line 30: change "hydrocarbyl," to -- hydrocarbyl; --.
Line 36: change "vinyl," to -- vinyl; --.
Line 62: change "hydrocarbyl," to -- hydrocarbyl; --.

Column 16,
Line 2: change "vinyl," to -- vinyl; --.
Line 23: change "$SbR_3.L$" to -- $SbR_3 \cdot L$ --.
Line 37: after "thioethers" insert -- ; --.
Line 38: change "tetrahydrofuran," to -- tetrahydrofuran; --.
Line 43: change "$SbR_3.L$" to -- $SbR_3L$ --.
Line 63: change "$SbR_3.L$" to $SbR_3 \cdot L$--.

Signed and Sealed this

Twenty-first Day of August, 2001

*Attest:*

*Nicholas P. Godici*

NICHOLAS P. GODICI
*Attesting Officer*       *Acting Director of the United States Patent and Trademark Office*